US005552885A

United States Patent [19]

Steen

[11] Patent Number: 5,552,885
[45] Date of Patent: Sep. 3, 1996

[54] MEASURING CHAMBER FOR FLOW CYTOMETER

[76] Inventor: Harald Steen, Wolffsgt. 3, Oslo N 0358, Norway

[21] Appl. No.: 343,466
[22] PCT Filed: Mar. 17, 1994
[86] PCT No.: PCT/EP94/00914
    § 371 Date: Nov. 22, 1994
    § 102(e) Date: Nov. 22, 1994
[87] PCT Pub. No.: WO94/22000
    PCT Pub. Date: Sep. 29, 1994

[30] Foreign Application Priority Data

Mar. 22, 1993 [IT] Italy .................. MI93A0539

[51] Int. Cl.⁶ .................................................. G01N 1/10
[52] U.S. Cl. .................... 356/246; 356/38; 356/73
[58] Field of Search ..................... 356/246, 244, 356/39, 73, 338, 336, 440; 250/573, 574, 576

[56] References Cited

U.S. PATENT DOCUMENTS

| | | | |
|---|---|---|---|
| 4,225,229 | 9/1980 | Gohde | 356/39 |
| 4,408,877 | 10/1983 | Lindmo et al. | 356/39 |
| 4,426,154 | 1/1984 | Steen | 356/73 |
| 4,756,427 | 7/1988 | Göhde et al. | 356/39 |
| 4,954,715 | 9/1990 | Zold | 250/461.1 |

FOREIGN PATENT DOCUMENTS

| | | | |
|---|---|---|---|
| 2853703 | 7/1980 | Germany . | |
| 0182549 | 8/1986 | Japan | 356/246 |
| 62-44647 | 2/1987 | Japan . | |
| 87/00628 | 1/1987 | WIPO . | |

*Primary Examiner*—Hoa Q. Pham
*Attorney, Agent, or Firm*—Darby & Darby, P.C.

[57] ABSTRACT

Measuring chamber for flow cytometer for the measuring of fluorescent and scattered light of individual cells or other microscopic particles, comprising: a body (2) with a flat surface (6), an inlet chamber (8) and an outlet chamber (10) within the body (2), which open on the surface (6), the chambers being positioned one in front of the other and being connected by a channel (12), the chamber (8) being equipped with an inlet tube (14) and an injection tube (16) and the chamber (10) being equipped with an outlet tube (18), a transparent plate (20) placed in front of the surface (6), and moveable from a first position detached from the surface to a second position in which the plate closes to seal the chambers (8, 10) and the channel (12), with optical means placed in front of the plate to direct light on a particle placed in the channel (12) and to receive fluorescent light emitted from the same particle, characterized by the fact that the axis of the tube (16) intersects the optical axis (30) of the optical means at a point outside the channel whereby a liquid and particles, injected into the chamber throughout the tube (14) and the tube (16) respectively, flow with laminal flow through the channel (12).

7 Claims, 1 Drawing Sheet

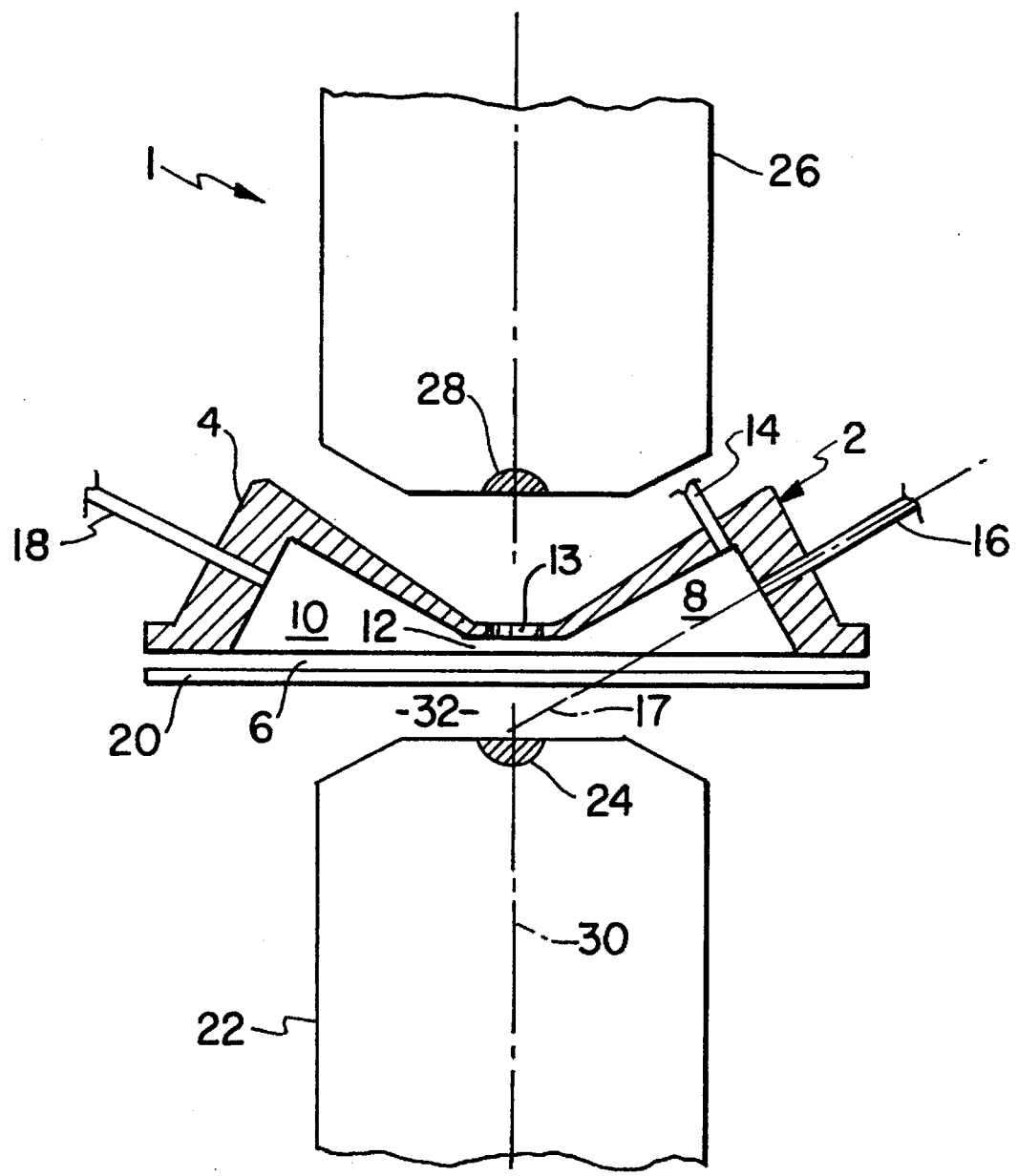

MEASURING CHAMBER FOR FLOW CYTOMETER

BACKGROUND OF THE INVENTION

The present invention refers to a measuring chamber for a flow cytometer to measure the fluorescent and scattered light of individual cells or microscopic particles, comprising: a body with a flat surface, an inlet chamber and an outlet chamber within the body, which open on the flat surface, the chambers being positioned one in front of the other and being connected by a channel in the body, the inlet chamber being equipped with an inlet tube and an injection tube and the outlet chamber being equipped with an outlet tube, a transparent plate placed in front of the flat surface, the plate being moveable from a first position detached from the flat surface to a second position in which the plate closes to seal the cheers and the channel, optical means placed in front of the transparent plate to direct light on the particle contained in the channel and receive fluorescent light emitted from the same particle.

In a flow cytometer, some biological cells or other types of microscopic particles are carried by a laminal flow of a liquid, like water, through the focus of an intense, luminous source. The fluorescent and scattered light emitted from each single cell when it passes through the focus are collected by suitable optical means and are directed onto proper light detectors.

The scattered light, obtained in this way, supplies information on the time and structure of the cell while the fluorescent light is a measure of the contents of the cell which had been previously colored with a fluorescent coloring substance which is bound to it in a particular manner.

To obtain the highest level of excitation possible at the focus and, consequently, the maximum sensitivity, the light is concentrated in a very small focus, usually with a length around 100 micrometers. The cells must follow the same route through the focus in order that they can be analyzed in a reproducable manner. To obtain this, the principle of "hydrodynamic foccussing" is used (P. J. Crossland-Taylor, Nature, Volume 171, Pgs. 37–38, 1953).

Hydrodynamic focussing is obtained in a cone nozzle, filled with water. The water, which is pumped in the nozzle, flows with laminal flow toward an opening at the pointed tip of the nozzle so as to form a lamina jet with a typical velocity of a few meters per second. The sample, that is, the suspension of the cells to be analyzed, is injected in the nozzle through a thin tube which has one of its end openings at or very close to the axis of the nozzle. Since the flow inside the nozzle is laminar, the sample is confined in the central part of the flow, both in the nozzle and the jet. Consequently, it follows a route of the jet that is always reproducible in an exact way. The cells are measured when this jet passes through the excitation focus. The principle of hydrodynamic focussing is used in all of the types of flow cytometers. In some cyometers, the opening of the nozzle connects with the atmospheric air, so that the emitted jet will contact said air. An inconvenience of this type of cytometer is that the user can come into contact with the noxious or infected substances.

In other types of cytometers, the opening connects with a narrow tube, preferably of rectangular section (known as "closed measuring chamber"). A significant inconvenience with this last type is that the thin tube is difficult to clean. However, this has the advantage that the user is protected from exposure to disinfecting and/or toxic agents present in the sample.

There are fundamentally two types of flow cytometers: those which use a laser as a source of light of excitation and those which use a high pressure arc lamp which contains xenon or mercury.

In the cytometers which use laser, the scattering of light can be measured in a direction close to that of the laser beam ("low angle light scattering"). This can also be measured at a right angle relative to the laser beam ("large angle light scattering") whereas the fluorescence is collected at a right angle to the laser beam. Said instruments can use either a nozzle that emits an air jet or in a closed measuring chamber.

The cytometers which use the arc lamps often have a microscope lens with oil immersion for the purpose of concentrating as much exciting light as possible on the flow containing the sample. The fluorescent light is usually collected with the same microscopic lens, which, thus, is called epimodal because it is adapted to collect also the fluorescent light emitted from the sample, while the scattered light of the sample can be highlighted in a dark field in the lower part of the cytometer (documents EP-A-0,229, 815, U.S. Pat. No. 4,915,501).

The existence of an open measuring chamber to use with cytometers which use an arc lamp is already known (EP-A-0,026,770). In this measuring chamber, a flow of the liquid is confined in a flat layer of water on the open surface of a microscope cover glass. The flow is observed from the opposite side through a microscope lens with oil immersion.

This type of measuring chamber has a serious inconvenience because it exposes the user to the risk of contamination by toxic and/or infected substances. Moreover, the functioning principle implies a limitation of the raze of sample flow, in some cases thereby limiting the measuring velocity.

On the other hand, this measuring chamber is the only one which allows for a precise measurement of the light scattering in cytometers which use arc lamps.

Other measuring chambers for this type of instruments do not permit an efficient measurement of the light scattering, which represents a serious limitation of their possibility of application (documents U.S. Pat Nos. 4,225,229 and 4,954, 715).

SUMMARY OF THE INVENTION

The object of the present invention is that of realizing a measuring chamber for a flow cytometer characterized in that the axis of the injection tube intersects the optical axis of the optical means at a point outside the channel whereby a liquid and some particles, injected into the inlet chamber throughout the inlet tube and the in section tube respectively, flow with laminar flow through the channel.

The advantages of the present invention will be clarified by the following description and by the sole diagrammatic figure of the annexed drawing, which illustrates the device of the invention from an axial section view.

DETAILED DESCRIPTION OF THE INVENTION

Referring to the drawing, reference numeral (1) indicates a flow cytometer. A fundamental part of the cytometer is the measuring chamber, which is comprised essentially of a body (4) preferably of circular form with a lower flat surface (6). In the body, there is an inlet chamber (8) and an outlet chaser (10), which open on the flat surface (6). The chambers (8, 10) are positioned one in front of the other and each chamber has a cross section which is reduced progressively when approaching the other chamber. In particular, in the form of the invention illustrated in the drawing, each chamber has the form of a semicone. The chambers are connected through a channel (12) which is inside the body (2).

The channel (12) preferably has a cross sectional rectangular form. On the bottom of the channel there is a transparent element (13) which generally is made of artificial quartz.

The inlet chamber (8) is equipped with an inlet tube (14) which serves to inject liquid under pressure into said chamber. Usually, this liquid consists of distilled or filtered water. Moreover, the chamber (8) is equipped with an injection tube (16) which serves to introduce cells or other microscopic matter to be analyzed into the measuring chamber. The tube (16) is moveable inside the body (2) along its axis (17) for reasons explained below.

The outlet chamber (10) is equipped with an outlet tube (18) which serves to eject water and the analyzed cells which entered through the tubes 14 and 16, respectively.

A transparent plate (20) is positioned in front of the flat surface (6) of the body (2). Also this plate is preferably made of artificial quartz. The plate is moveable from a first position in which it is detached from the flat surface (as illustrated in the drawing) to a second position in which it is lying against the surface and closed to seal the inlet chamber (8), the outlet chamber (10) and the channel (12).

The cytometer is further equipped with optical means to direct the light against a particle contained in the channel (12) and to receive the fluorescent light emitted by the same particle. Usually, these optical means are comprised of a microscope objective (22) which is placed in front of the transparent plate (20). The microscope lens is equipped with a lens (24) which serves to concentrate the light emitted from a light source, in this case an arc lamp (not illustrated), on the particle contained in the channel (12). It is observed that the position of the body (2) can be moved closer to or further away from the lens (24) through suitable means so that the focus of the lens falls on the interior of the channel (12).

The volume comprised between the transparent plate (20) and the extremity of the microscope objective (22) is filled with the corresponding immersion oil which serves to adjust the refractive index of the lens (24) to the refractive index of the material which makes up the plate.

The cytometer (1) is further equipped with a second microscope objective (26) placed on the other side with respect to the first microscope objective (22) relative to the body (2). The microscope objective (26) is also equipped with an objective (28) placed in front of the transparent element (13). The lens (24) and the lens (28) are on the same optical axis (30) The function of the second microscope objective (26) will be clarified below.

The operation of the measuring chamber of the flow cytometer is the following:

Through the inlet tube (14), distilled or filtered water is introduce and some cells to be analyzed are injected throughout the injection tube (16). The tube (16) is positioned inside the chamber (8) in such a way that its axis intersects the optical axis (30) at a point (32) outside the channel (12), in this way a laminar flow can be realized, made of liquid and some particles in the channel (12). Thanks to the laminar flow, it is possible, through the microscope objectives (22 and 26), to analyze the cells one by one on the inside of the same channel. In fact, while a cell passes through the channel, the light emitted on it is concentrated by the first microscope objective (22). The cell diffracts the light rays in all directions and emits a fluorescent light which is collected again by the first microscopic objective. Only one part of the diffracted rays, that is, those which form particular angles with respect to the optical axis (30), are able to pass through the transparent element (13) and are collected by the second microscope objective (26). The second microscope objective, in turn, transmits these rays to determined known devices, which carry out the analysis of the characteristics of the cell, such as size, granulation and structure.

As the point of intersection of the axis (17) of the tube (16) with the optical axis (30) lies outside the channel (12), it is possible to move the flow of the cells to be analyzed in the channel in the direction of the optical axis, merino the tube (16) along its axis. Thus, the flow can be positioned in a way to pass exactly through the focus of the microscope objective (22) without moving the cell relative to this microscope objective. In this way, the layer of the immersion oil provided between the microscope objective (22) and the transparent plate (20) can be maintained very thin to reduce the background fluorescent light which is emitted from the same oil and, thus, the disturbance caused by this is reduced. Thus, the object of the invention has been attained, which is that of sending the flow against the transparent plate and not in the true and same measuring point which is found on the inside of the channel (12), because only in this way is it possible to get a laminar flow and, thus, an accurate reading of the movement of the particles along the focal plane.

I claim:

1. A measuring chamber for a flow cytometer for measurement of fluorescent light and scattered light of individual cells and other microscopic particles, said measuring chamber comprising:

a body with a flat surface;

an inlet chamber and an outlet chamber in said body which open on said flat surface, said chambers being positioned one in front of the other and connected by a channel in said body, the inlet chamber being equipped with an inlet tube and the outlet chamber being provided with an outlet tube;

an injection tube within said inlet chamber, said injection tube having a longitudinal axis and being moveable along said longitudinal axis inside said inlet chamber;

a transparent plate placed in front of said flat surface; and optical means placed in front of the transparent plate to direct light against the particle contained in the channel and to receive fluorescent light emitted by the particle, said optical means having an optical axis;

said measuring chamber characterized in that said longitudinal axis of said injection tube intersects said optical axis at a point outside said channel whereby a liquid and some particles injected into said inlet chamber through said inlet tube and said injection tube, respectively, flow with laminar flow through said channel.

2. Chamber according to claim 1, characterized in that said transparent plate is moveable between a first position detached from the flat surface and a second position in which said transparent plate closes said flat surface to seal said inlet and outlet chambers and said channel.

3. Chamber according to claim 1, characterized in that each chamber has a cross section which reduces as it approaches the other chamber.

4. Chamber according to claim 3, characterized in that each chamber has a semicone form.

5. Chamber according to claim 1, characterized in that the liquid is distilled or filtered water.

6. Chamber according to claim 1, characterized in that the position of said body can be regulated in a plane perpendicular to said optical axis so as to bring said channel in the focus of said optical means.

7. Chamber according to claim 1, characterized in that said optical means consist of first and second opposing microscope objectives.

* * * * *

UNITED STATES PATENT AND TRADEMARK OFFICE
CERTIFICATE OF CORRECTION

PATENT NO. : 5,552,885
DATED : September 3, 1996
INVENTOR(S) : Harald STEEN

It is certified that error appears in the above-indentified patent and that said Letters Patent is hereby corrected as shown below:

Title page, [30], Foreign Application Priority Data, change "MI93A0539" to --MI93A000539--.

Signed and Sealed this

Eighth Day of April, 1997

Attest:

BRUCE LEHMAN

Attesting Officer

Commissioner of Patents and Trademarks